(12) United States Patent
Siejko et al.

(10) Patent No.: US 8,319,648 B2
(45) Date of Patent: Nov. 27, 2012

(54) SYSTEM AND METHOD FOR DETECTION OF HF DECOMPENSATION BASED ON SIGNS AND SYMPTOMS

(75) Inventors: Krzysztof Z. Siejko, Maple Grove, MN (US); Viktoria A. Averina, Roseville, MN (US); Abhilash Patangay, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 527 days.

(21) Appl. No.: 12/563,882

(22) Filed: Sep. 21, 2009

(65) Prior Publication Data

US 2010/0073170 A1    Mar. 25, 2010

Related U.S. Application Data

(60) Provisional application No. 61/098,858, filed on Sep. 22, 2008.

(51) Int. Cl.
*G08B 23/00* (2006.01)
(52) U.S. Cl. .............. 340/573.1; 340/539.1; 340/286.06
(58) Field of Classification Search ............... 340/573.1, 340/539.1, 539.11–539.12, 286.06, 286.07
See application file for complete search history.

(56) References Cited

U.S. PATENT DOCUMENTS

| | | | |
|---|---|---|---|
| 4,686,987 A | 8/1987 | Salo et al. | |
| 5,284,136 A | 2/1994 | Hauck et al. | |
| 5,342,406 A | 8/1994 | Thompson | |
| 6,076,015 A | 6/2000 | Hartley et al. | |
| 6,556,977 B1 | 4/2003 | Lapointe et al. | |
| 6,666,826 B2 | 12/2003 | Salo et al. | |
| 6,678,669 B2 | 1/2004 | Lapointe et al. | |
| 6,821,249 B2 | 11/2004 | Casscells, III et al. | |
| 7,127,290 B2 | 10/2006 | Girouard et al. | |
| 7,149,576 B1 | 12/2006 | Baura et al. | |
| 7,382,247 B2* | 6/2008 | Welch et al. | 340/539.12 |
| 7,558,622 B2* | 7/2009 | Tran | 600/509 |

(Continued)

FOREIGN PATENT DOCUMENTS

WO   WO-2010/033928 A1    3/2010

OTHER PUBLICATIONS

"International Application Serial No. PCT/US2009/057710, International Search Report mailed Dec. 4, 2009", 6 pgs.

(Continued)

*Primary Examiner* — Daniel Previl
(74) *Attorney, Agent, or Firm* — Schwegman Lundberg & Woessner, P.A.

(57) ABSTRACT

In an example, physiologic information about a patient can be obtained and mapped to a first set of fuzzy logic membership functions, and a symptom status can be derived from the mapping of the physiologic information using a first fuzzy logic inference. In an example, the symptom status can be mapped to a second set of fuzzy logic membership functions, and a disease status can be derived from the mapping of the symptom status to the second set of fuzzy logic membership functions using a second fuzzy logic inference.

20 Claims, 7 Drawing Sheets

U.S. PATENT DOCUMENTS

| | | |
|---|---|---|
| 2003/0008407 A1 | 1/2003 | Fu |
| 2003/0092975 A1 | 5/2003 | Casscells, III et al. |
| 2003/0125774 A1 | 7/2003 | Salo |
| 2004/0127792 A1* | 7/2004 | Siejko et al. ............ 600/439 |
| 2006/0010090 A1 | 1/2006 | Brockway et al. |
| 2006/0161069 A1 | 7/2006 | Li |
| 2006/0224067 A1* | 10/2006 | Giftakis et al. ........... 600/483 |
| 2006/0265022 A1* | 11/2006 | John et al. ............... 607/45 |
| 2007/0260285 A1 | 11/2007 | Libbus et al. |
| 2007/0299356 A1 | 12/2007 | Wariar et al. |
| 2008/0177194 A1 | 7/2008 | Zhang et al. |
| 2008/0262533 A1* | 10/2008 | McEwen et al. ............ 606/202 |
| 2010/0094102 A1 | 4/2010 | Zhang et al. |

OTHER PUBLICATIONS

"International Application Serial No. PCT/US2009/057710, Written Opinion mailed Dec. 4, 2009", 9 pgs.

Wang, C, S., et al., "Does This Dyspneic Patient in the Emergency Department Have Congestive Heart Failure?", *Journal of the American Medical Association*, 294(15), (2005), 1944-1956.

"European Application Serial No. 09792791.7, Office Action mailed Nov. 29, 2011", 5 pgs.

"European Application Serial No. 09792791.7, Response filed Mar. 28, 2012 to Office Action mailed Nov. 29, 2011", 6 pgs.

* cited by examiner

SYSTEM AND METHOD FOR DETECTION OF HF DECOMPENSATION BASED ON SIGNS AND SYMPTOMS

CROSS-REFERENCE TO RELATED APPLICATION

This application claims the benefit of U.S. Provisional Application No. 61/098,858, filed on Sep. 22, 2008, under 35 U.S.C. §119(e), which is hereby incorporated by reference.

BACKGROUND

A body can be thought of as a group of systems working together to maintain a person's health. For example, the circulatory system can be responsible for providing oxygen and nutrients to various organs. The heart can be thought of as the central organ of the circulatory system. The left portions of the heart can draw oxygenated blood from the lungs and supply it to other parts of the body. The body can use the oxygenated blood as part of a metabolic cycle. The metabolic cycle can partially deoxygenate the blood while providing energy to organs or muscle tissue. The right portions of the heart can then return such deoxygenated blood to the lungs where the blood can become oxygenated again.

A variety of physiologic conditions can affect the mechanical or electrical behavior of the heart. A disease such as heart failure ("HF") can reduce the pumping capability or efficiency of the heart. As congestive heart failure progresses, the reduced pumping capability or efficiency of the heart can cause other undesirable symptoms, such as edema (retention of body fluid), weight gain, shortness of breath, poor exercise tolerance, sleeping related problems, or other undesirable symptoms, and can ultimately lead to death.

OVERVIEW

In an example, physiologic information about a patient can be obtained and mapped to a first set of fuzzy logic membership functions, and a symptom status can be derived from the mapping of the physiologic information using a first fuzzy logic inference. In an example, the symptom status can be mapped to a second set of fuzzy logic membership functions, and a disease status can be derived from the mapping of the symptom status to the second set of fuzzy logic membership functions using a second fuzzy logic inference.

In Example 1, a system includes a physiologic monitor configured to obtain physiologic information about a patient, a processor coupled to the physiologic monitor and configured to receive the physiologic information about the patient, the processor comprising: a symptom status detector including a first fuzzy logic inference module configured to derive a symptom status from the physiologic information using a first fuzzy logic inference, and a disease status detector coupled the symptom status detector, the disease status detector including a second fuzzy logic inference module configured to derive a disease status from the symptom status using a second fuzzy logic inference.

In Example 2, the disease status detector of Example 1 is optionally configured to detect a heart failure decompensation status.

In Example 3, the system of any one or more of Example 1 or Example 2 optionally includes a physiologic sensor coupled to the physiologic monitor, wherein the physiologic sensor includes at least one of a weight scale, an electrocardiogram (ECG) sensor, a respiration sensor, a heart sound sensor, a blood pressure sensor, an accelerometer, or an intrathoracic impedance sensor.

In Example 4, the system of any one or more of Examples 1-3 optionally includes a display coupled to the processor, the display configured to report at least one of the symptom status or the heart failure decompensation status to a user.

In Example 5, the system of any one or more of Examples 1-4 optionally includes a user input coupled to the processor, the user input configured to receive at least some of the physiologic information from a user in response to a query including whether the patient has experienced at least one of a shortness of breath, an abnormal fatigue, an abnormal pain, an abnormal swelling, a chronic cough, a decreased appetite, or a need for an extra pillow when sleeping.

In Example 6, the system of any one or more of Examples 1-5 optionally includes a fuzzy logic rule selector configured to select at least one rule using information about whether at least one physiologic sensor is unreliable or unavailable, and wherein the first fuzzy logic inference module is optionally configured to derive the symptom status in response to and using the at least one selected rule.

In Example 7, a method includes obtaining physiologic information about a patient, mapping the physiologic information to a first set of fuzzy logic membership functions, deriving a symptom status from the mapping of the physiologic information to the first set of fuzzy logic membership functions using a first fuzzy logic inference, mapping the symptom status to a second set of fuzzy logic membership functions, and deriving a disease status from the mapping of the symptom status to the second set of fuzzy logic membership functions using a second fuzzy logic inference.

In Example 8, the deriving the disease status of Example 7 optionally includes deriving a heart failure decompensation status.

In Example 9, the obtaining the physiologic information of any one or more of Examples 7 or 8 optionally includes monitoring at least one of an implantable or an external physiologic sensor.

In Example 10, the obtaining the physiologic information of any one or more of Examples 7-9 optionally includes obtaining information derived from at least one of a heart rate, a respiration rate, a respiration timing, a blood pressure, a lung tidal volume, a physical activity level, a weight, an intrathoracic impedance, a heart sound timing, or a heart sound magnitude.

In Example 11, the deriving the symptom status using the first fuzzy logic inference of any one or more of Examples 7-10 optionally includes selecting a rule using information about whether at least one physiologic sensor is unreliable or unavailable, and deriving the symptom status using the selected rule.

In Example 12, the method of any one or more of Examples 7-11 optionally includes querying a user for at least some of the physiologic information, wherein the query includes at least one of whether the patient has experienced shortness of breath, abnormal fatigue, abnormal pain, abnormal swelling, a chronic cough, a decreased appetite, or a need for an extra pillow when sleeping, and receiving a user response including at least some of the physiologic information.

In Example 13, the deriving the symptom status of any one or more of Examples 7-12 optionally includes deriving at least one of a dyspnea score, a fluid overload index, a left ventricular filling pressure index, a fatigue index, or a cardiac output index.

In Example 14, the method of any one or more of Examples 7-13, optionally includes displaying at least one of the symptom status or the heart failure decompensation status to a user.

In Example 15, the method of any one or more of Examples 7-14, optionally includes providing an alert to a user when the heart failure decompensation status indicates an onset of acute heart failure decompensation.

In Example 16, the at least one membership function included in the first or second sets of fuzzy logic membership functions of any one or more of Examples 7-15 is optionally categorized by a linguistic term.

In Example 17, the linguistic term of any one or more of Examples 7-16 optionally includes at least one of very low, low, medium, high, or very high.

In Example 18, the linguistic term of any one or more of Examples 7-17 optionally classifies at least one of the physiologic information or the symptom status by a degree of change from a baseline.

In Example 19, the linguistic term of any one or more of Examples 7-18 optionally classifies at least one of the physiologic information or the symptom status by a rate of change.

In Example 20, the at least one of the first or second fuzzy logic inferences of any one or more of Examples 7-19 optionally uses at least one rule based on information obtained from historical patient data.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In an example, one or more systems or methods can be used to monitor various physiologic parameters to predict a worsening heart failure status of a patient. A sudden worsening of HF-related symptoms can be referred to as acute heart failure decompensation ("AHFD"). A person having heart failure can sometimes be unaware of such changes in physiologic status. Automatic warning or alert generation systems or methods can assist in early identification of a worsening condition or other significant disease events. Treatment of HF can then be initiated or modified. Treatment can include initiating or modifying pharmacological therapy, cardiac resynchronization therapy (e.g., using an implantable device such as a cardiac rhythm management device), physiologic monitoring (e.g., through one or more sensors), or the like. Early detection of worsening heart failure can reduce the frequency or length of hospitalization, improve quality of life, or reduce health care costs.

The present inventors have recognized, among other things, that using multiple sources of physiologic information, such as one or more sensors or questionnaires, can increase the accuracy or specificity of detecting or predicting the onset of AHFD. As the number of sensors or questions increases, it can become problematic to combine such information into an actionable summary for a patient, clinician, or caregiver. The present inventors have also recognized that a fuzzy logic inference can be used to simplify an analysis of physiologic information obtained from the multiple sources, such as the one or more sensors, or to derive one or more symptoms from such physiologic information. The present inventors have also recognized that using a "cascaded" fuzzy logic approach can provide both intermediate information to a clinician regarding symptom status or severity for the one or more symptoms, as well as describe an overall disease status for the one or more diseases (e.g., heart failure, diabetes, or one or more other diseases). In an example, the cascaded fuzzy logic approach can include using a second fuzzy logic inference to derive a status for one or more diseases from a status of one or more symptoms. In an example, the status (e.g., a description, or degree of severity, or other status) of the one or more inferred symptoms can include one or more status generally used by a clinician, a patient, or other user in a clinical diagnosis. In certain examples, the clinician, the patient, or the other user can be provided with actionable summary information in a more intuitive form using plain language (e.g., linguistic terms) to describe both the status of one or more symptoms, and the status of one or more diseases.

Figure 1:
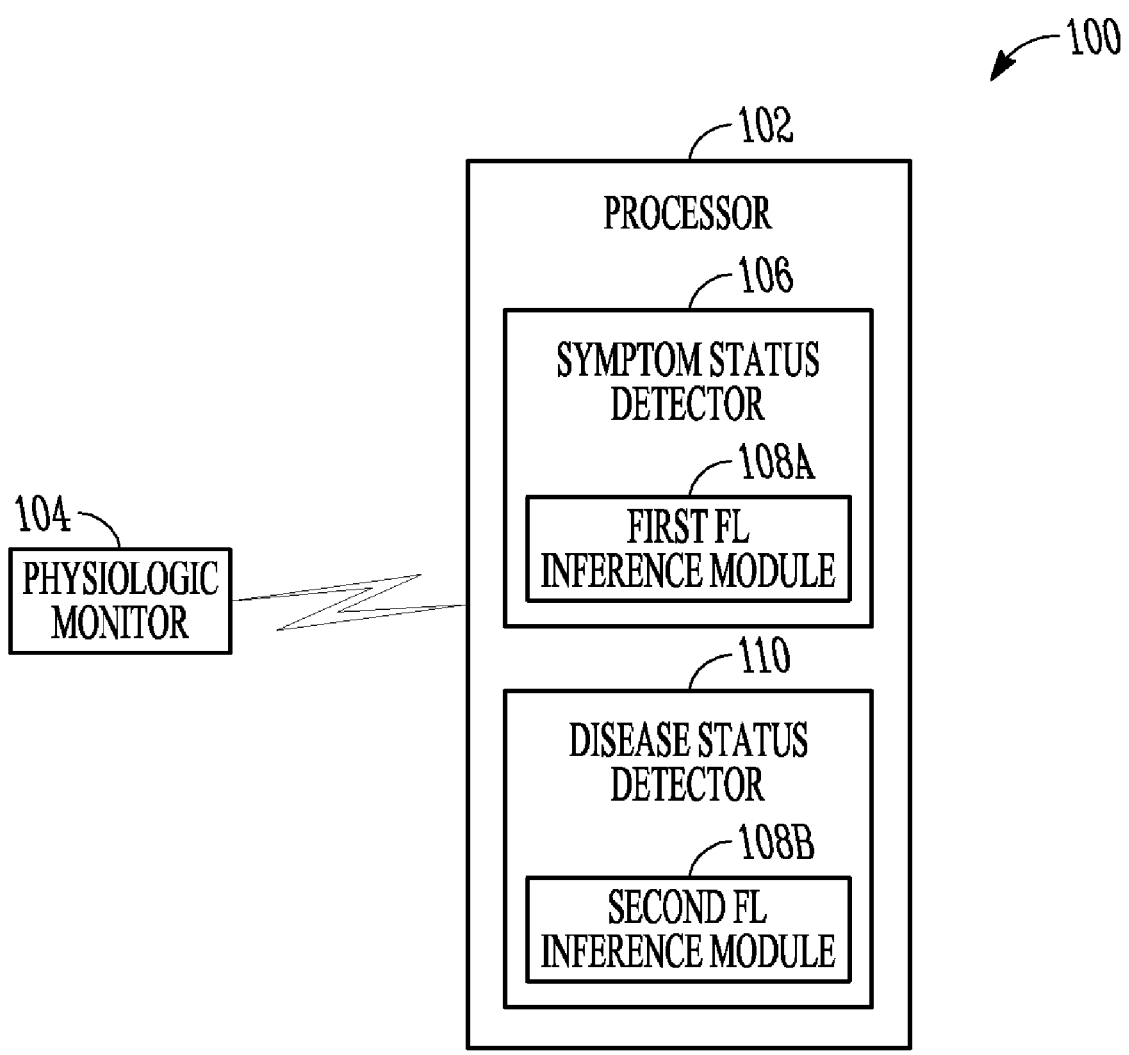
FIGS. 1-3 illustrate generally examples of a system for detecting a status of one or more diseases.

FIG. 1 illustrates generally an example of a system 100 for detecting a status of one or more diseases. In this example, the system 100 can include a physiologic monitor 104 and a processor 102. In an example, the physiologic monitor 104 can be configured to obtain, sense, or detect physiologic information about a patient (or other person).

In an example, the processor 102 can be communicatively coupled to the physiologic monitor 104, and can be configured to receive the physiologic information from the physiologic monitor 104. In certain examples, the processor 102 can include a symptom status detector 106 and a disease status detector 110. In an example, the symptom status detector 106 can include a first fuzzy logic inference module 108A configured to derive a status for one or more symptoms from the physiologic information obtained from one or more sensors. In an example, the disease status detector 110 can include a second fuzzy logic inference module 108B configured to derive a status for one or more diseases from the status for the one or more symptoms. In other examples, more than two layers of cascaded fuzzy logic inferences or less than two layers of cascaded fuzzy logic inferences can be made. In an example, one or more sensors can be communicatively coupled to the physiologic monitor 104, and the one or more sensors can use a fuzzy logic inference to detect, determine, or receive the physiologic information about the patient or other person.

Figure 2:
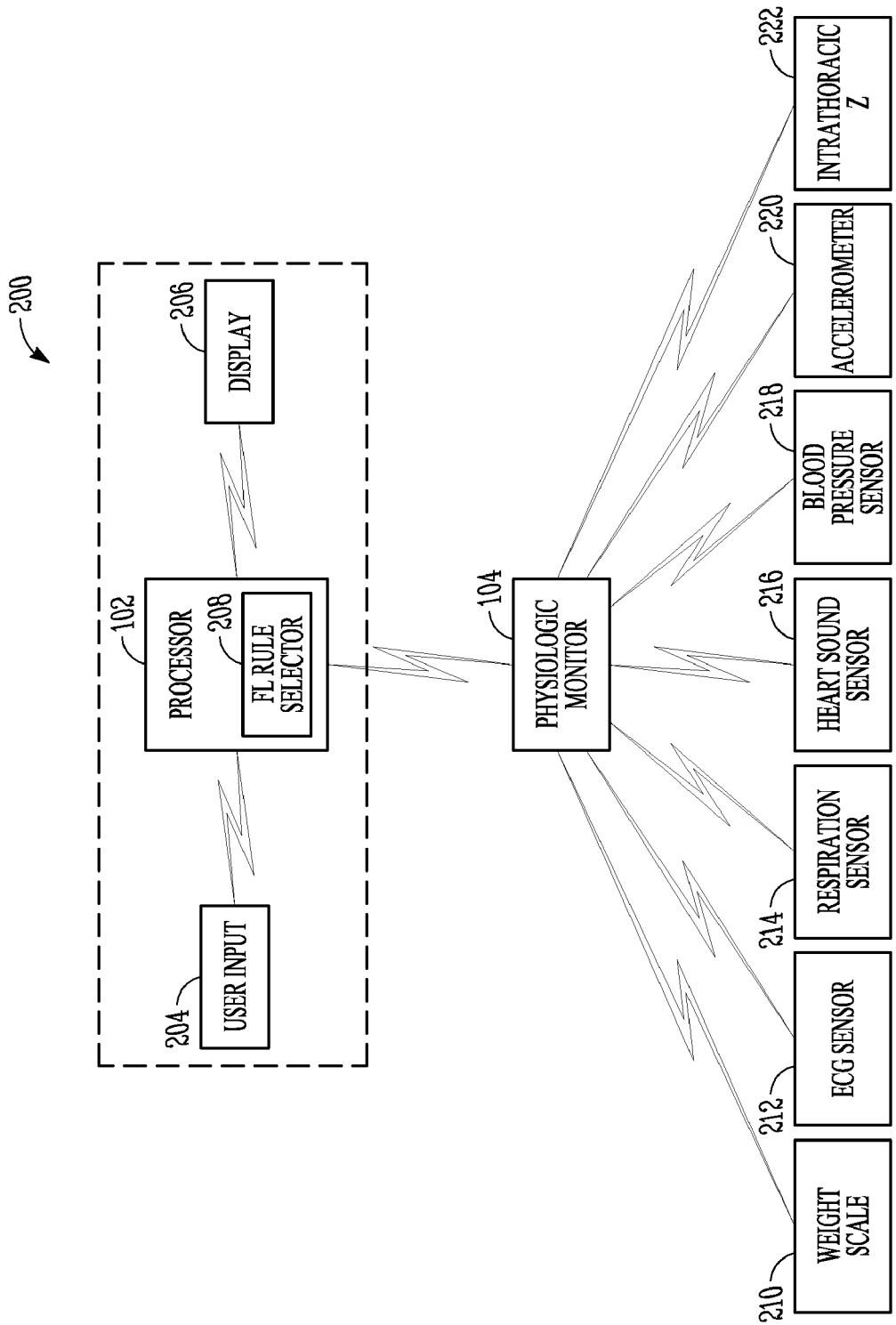

FIG. 2 illustrates generally an example of a system 200 for detecting a status of one or more diseases. In this example, the system 200 can include a physiologic monitor 104 communicatively coupled to a processor 102. In an example, the system 200 can include a display 206 and a user input 204. In this example, the display 206 and the user input 204 can be communicatively coupled to the processor 102. In an example, one or more displays (e.g., the display 206) or one or more user inputs (e.g., the user input 204) can be communicatively coupled to the physiologic monitor 104 or the processor 102.

In the example of FIG. 2, the physiologic monitor 104 can be coupled to or can include one or more sensors, such as a weight sensor 210 (e.g., a scale external to a patient), an electrocardiogram sensor 212 ("ECG"), a respiration sensor 214, a heart sound sensor 216, a blood pressure sensor 218 (e.g., a blood pressure cuff or an implantable sensor), an accelerometer 220 (e.g., a piezoelectric sensor or one or more other acceleration or position sensors), or an intrathoracic impedance ("Z") sensor 222, or one or more other sensors (e.g., an implantable or an external blood glucose monitor).

In an example, one or more displays (e.g., the display 206) can be configured to report a status of one or more symptoms or a status of one or more diseases to a user. In certain examples, the status of the one or more symptoms or diseases can be delivered to the user via an electronic communication (e.g., a message on a display, an electronic mail message, an audible alarm, a telephone message, a user-accessible world wide web application, etc.). In certain examples, the status of the one or more symptoms or diseases can be delivered as a warning, an alert, an alarm, as a chronic or ambulatory report, or in one or more other forms. In an example, physiologic information about the one or more sensors can be reported to the user, and the physiologic information can include one or more data values, one or more trends, one or more statistics (a maximum, minimum, moving average, weighted average, median, mean, or another central tendency of sensor data), or one or more other forms of summary information.

In an example, the processor 102 can include a fuzzy logic rule selector 208. In certain examples, the fuzzy logic rule selector 208 can be configured to select one or more fuzzy logic inferences or one or more other fuzzy logic rules using information provided by the physiologic monitor 104 (e.g., a rule system of one or more rules or fuzzy sets established using a Mamdani-type method, or a Sugeno-type method, or another method). In an example, if one or more sensors are unreliable or unavailable, the fuzzy logic rule selector 208 can be configured to select the one or more fuzzy logic inferences or rules to avoid using missing or incorrect physiologic information to derive the status of the one or more symptoms.

In an example, the display 206 can be configured to display a query to the user. In certain examples, the query can include one or more of whether a patient has experienced at least one of a shortness of breath, an abnormal fatigue, an abnormal pain, an abnormal swelling, a chronic cough, a decreased appetite, a need for an extra pillow when sleeping, or one or more other patient or user queries, and the user input 204 can be configured to receive at least some of the physiologic information from the user in response to the query.

In certain examples, the processor 102, the physiologic monitor 104, the display 206, the user input 204, or the one or more sensors can be a component, portion, or part, of an external assembly, such as a computer server, a personal computer (e.g., a physician programmer assembly for use in communication with an implantable medical device), a hand-held electronic assembly (e.g., a personal digital assistant or other assembly), an external patient monitoring assembly (e.g., a bed-side monitor located in a person's home), or one or more other external medical devices. In certain examples, the processor 102, the physiologic monitor 104, or the one or more sensors can be a component, portion, or part of an implantable assembly, such as an implantable medical device ("IMD").

Figure 3:
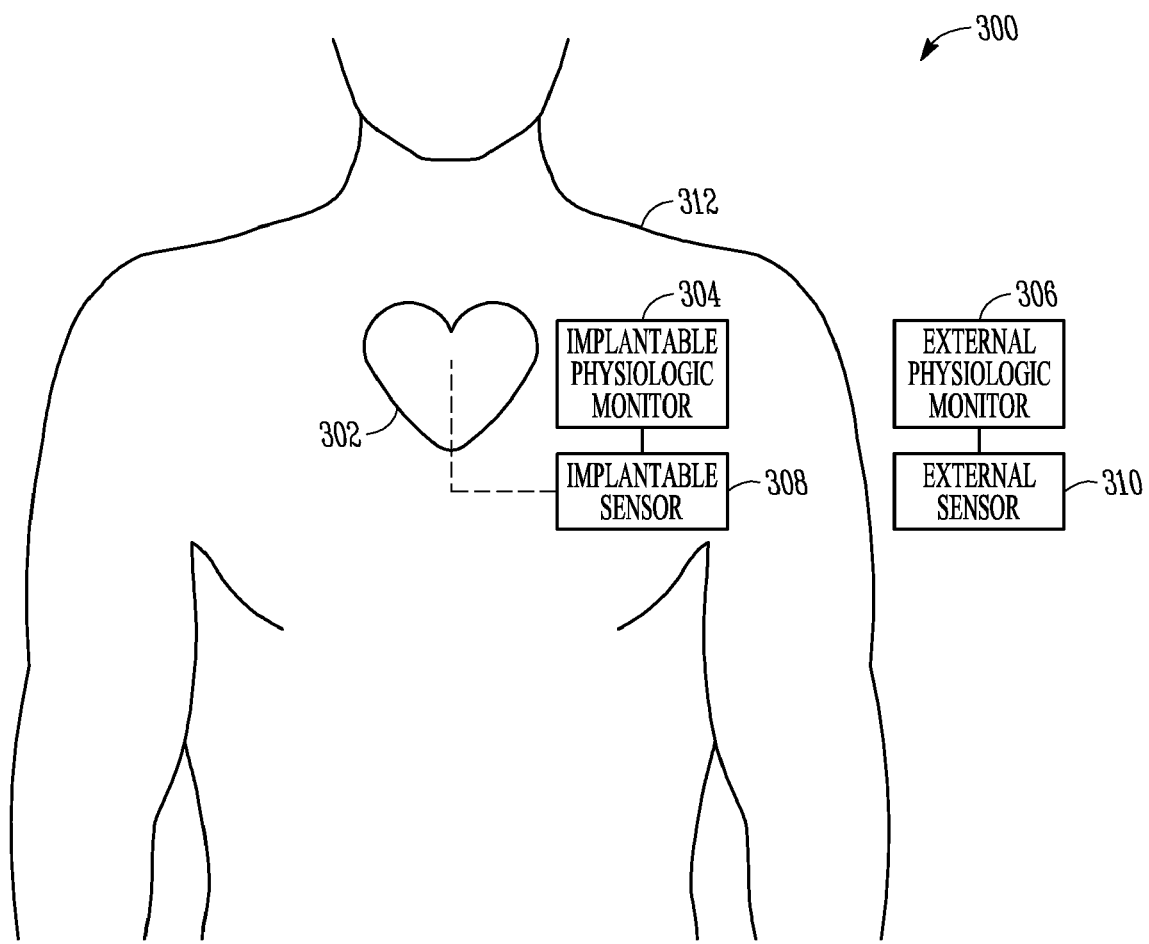

FIG. 3 illustrates generally an example of a system 300 for detecting a status of one or more diseases or symptoms. In certain examples, the system 300 can include an implantable physiologic monitor 304 communicatively coupled to an implantable sensor 308, or the system 300 can include an external sensor 310 communicatively coupled to an external physiologic monitor 306. In an example, one or more implantable sensors (e.g., the implantable sensor 308), or the implantable physiologic monitor 304 can be a component, portion or part of an IMD. In an example, the IMD can be a cardiac rhythm management ("CRM") device, and can include one or more of cardiac resynchronization therapy delivery circuitry, pacing circuitry, or tachyarrhythmia therapy circuitry (e.g., antitachyarrhythmic pacing or defibrillation shock). In an example, the CRM device can be implanted in a person 312. In an example, one or more additional sensor assemblies (e.g., an intravascular pressure sensor) can be implanted in the person 312, and can communicate with either the implantable physical monitor 304 or with one or more other implantable or external devices. In certain examples, an IMD assembly can include a processor 102, one or more sensors (e.g., the implantable sensor 308), the implantable physical monitor 304, or one or more other components, portions, or modules. In the example of FIG. 3, the implantable sensor 308 can be coupled to a heart 302 via one or more leads, and can include one or more of a blood pressure sensor, an intrathoracic impedance sensor, a respiration sensor (e.g., capable of sensing respiration rate, respiration timing, lung tidal volume, minute ventilation, or one or more other respiratory parameters), an acoustic sensor (e.g., to detect heart sounds), an activity level sensor (e.g., an accelerometer to detect a person's physical activity), an electrocardiogram sensor, or one or more other implantable sensors. In certain examples, the external sensor 310 can include at least one of the blood pressure sensor, the respiration sensor, the weight scale, or one or more other external sensors.

Figure 4:
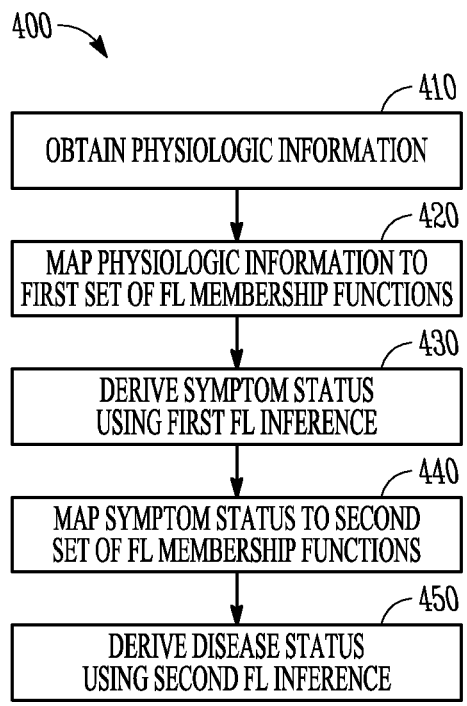
FIG. 4 illustrates generally an example of a method for deriving a disease status from physiologic information using a first and a second fuzzy logic inference.

FIG. 4 illustrates generally an example of a method 400 for deriving a disease status from physiologic information using a first and a second fuzzy logic inference. At 410, physiologic information about a patient can be obtained, such as by monitoring one or more implantable or external sensors (e.g., using an implantable physiologic monitor 304, an implantable sensor 308, an external sensor 310, or an external physiologic monitor 306). At 420, the physiologic information can be mapped to a first set of fuzzy logic ("FL") membership functions. In an example, physiologic information can be obtained from one or more sensors or queries. At 430, a first fuzzy logic inference can be used to derive a status of one or more symptoms using the mapping of the physiologic information. At 440, the resulting status of one or more symptoms can be mapped to a second set of fuzzy logic membership functions. At 450, a second fuzzy logic inference can be used to derive a status of one or more diseases using the mapping of the one or more symptoms.

In certain examples, the first or second set of fuzzy logic membership functions can be defined by one or more data values, one or more trends (e.g., a direction of change, a rate of change, a moving average, median, mean, or other central tendency, a count of one or more events, a degree of change from a baseline value such as an average, or other trend), one or more measures of a dispersion of a population of data (e.g., a variance, a standard deviation, or other measure), or other information (e.g., a response to a query such as a boolean value).

Figure 5:
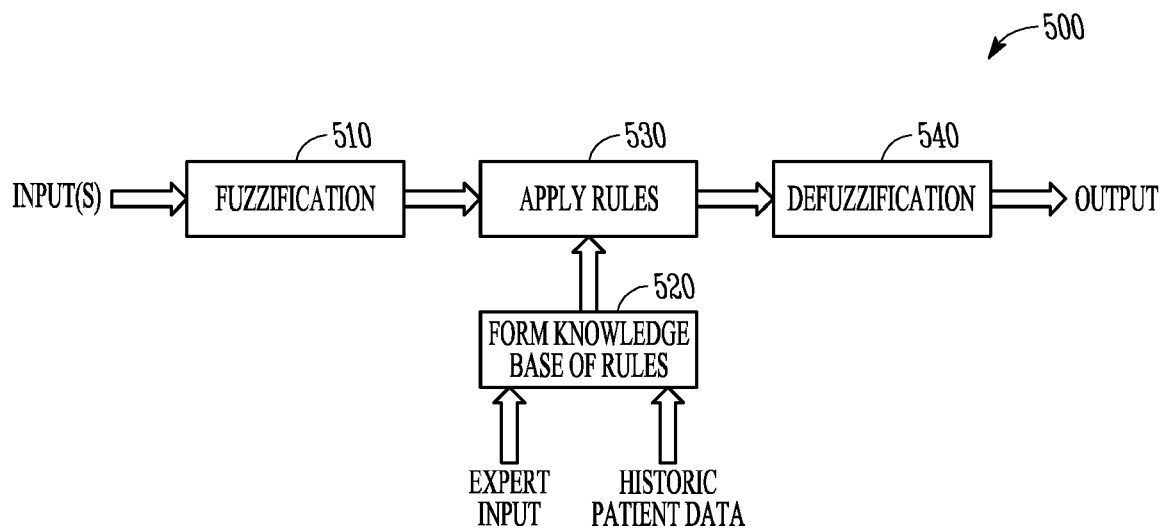
FIG. 5 illustrates generally an example of a method for performing a fuzzy logic inference.

FIG. 5 illustrates generally an example of a method 500 for performing a fuzzy logic inference. At 510, one or more inputs (e.g., physiologic information from one or more sensors, a status of one or more symptoms, or other information) can be "fuzzified." Fuzzifying the one or more inputs can include assigning information from the one or more inputs (e.g., one or more data values, trends, etc.) to one or more input fuzzy sets described by one or more membership functions. In FIG. 5, at 520, expert input or historic patient data can be combined into a knowledge base. In certain examples, the knowledge base can be converted into a set of one or more rules. In an example, the one or more rules can relate each of the one or more fuzzified inputs (e.g., an input fuzzy set) to one or more output fuzzy sets using one or more fuzzy operators (e.g., a fuzzy "AND," a fuzzy "OR," or one or more other operators). In the example of FIG. 5, at 530, the one or more rules can be applied exhaustively to the one or more fuzzified inputs. At 540, the one or more output fuzzy sets resulting from the application of the one or more rules can include one or more output functions, and the resulting output functions can be aggregated and "defuzzified." In an example, the aggregation method can use a maximum, sum, or other operator to combine the one or more output fuzzy sets (e.g., one or more output functions) into an aggregate function. In certain examples, defuzzifying the one or more output fuzzy sets can provide a numeric value as an output. In an example, one or more numeric outputs from one or more fuzzy logic inferences can be used as an input to another different fuzzy logic inference.

In certain examples, the rule set can be defined by trial and error, such as by using a neural network, by using a method similar to a Mamdani-type method (e.g., FIG. 9), by using a method similar to a Sugeno-type method, or by using one or more other methods. In a Sugeno-type method, the one or more output fuzzy sets can include linear or constant output functions. The Sugeno-type method can reduce an amount of computation required for defuzzification at 540 compared to a Mamdani-type method (e.g., an integration can be used for a centroid computation on the aggregate function and can be simpler using the Sugeno-method). In a Mamdani-type method (e.g., FIG. 9), the one or more fuzzy output fuzzy sets need not include linear or constant output functions.

Figure 6:
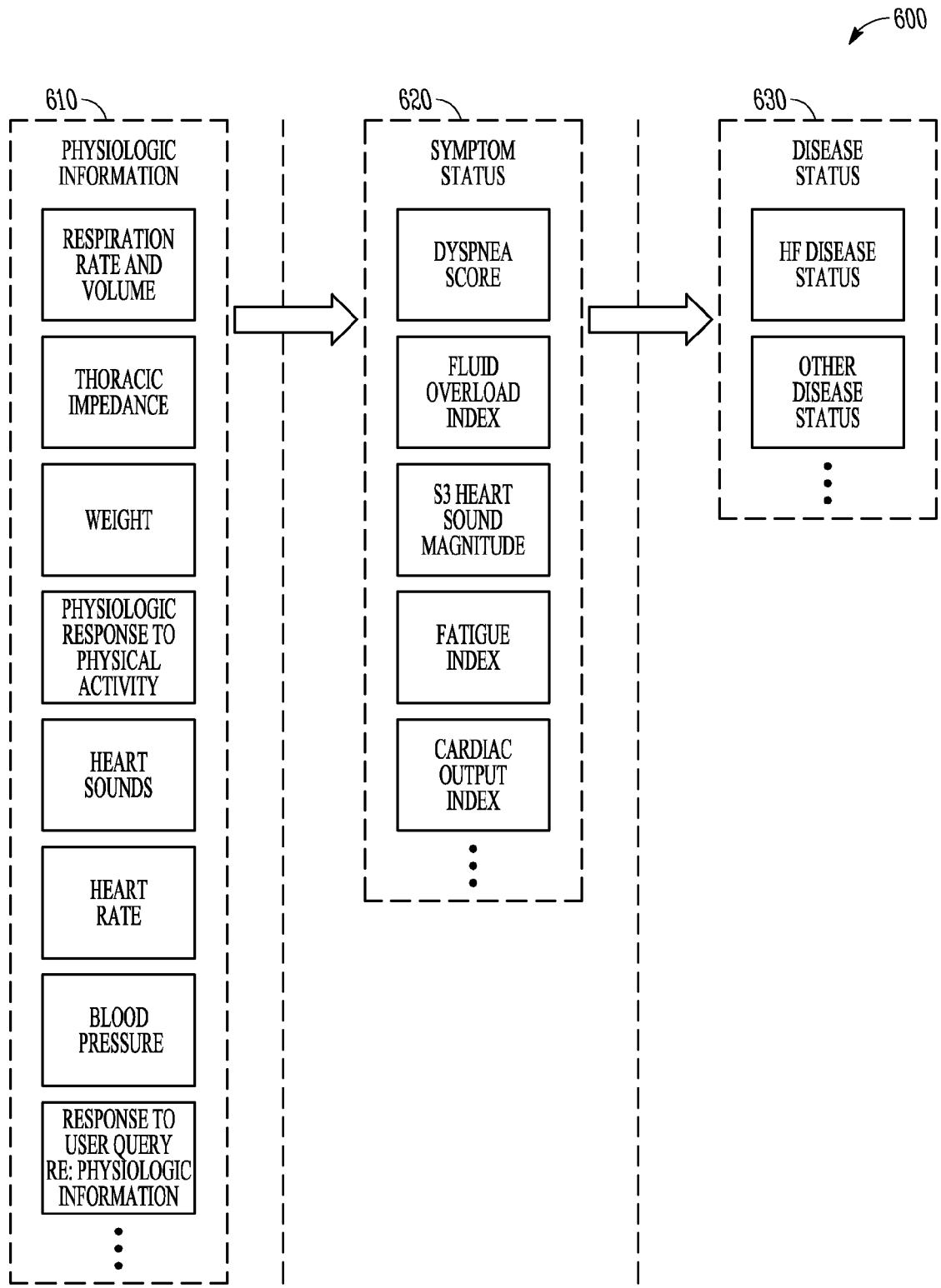
FIG. 6 illustrates generally a diagram showing a example of a relationship between one or more sources of physiologic information, a symptom status for one or more symptoms, and a disease status for one or more diseases.

FIG. 6 illustrates generally a diagram 600 showing a relationship between one or more sources of physiologic information 610, a symptom status for one or more symptoms 620, and a disease status for one or more diseases 630. In this example, the physiologic information 610 can be obtained from one or more sensors and can include heart rate information, respiration rate information, respiration timing information, blood pressure information, lung tidal volume (e.g., respiration volume) information, physical activity level information, exercise tolerance information (e.g., a patient's physiologic response to physical activity), weight information, intrathoracic impedance information (e.g., to assess fluid build-up, to monitor respiration-related parameters, or to monitor cardiac-related parameters), heart sound timing information, heart sound magnitude information (e.g., an S3 heart sound magnitude), or other information (e.g., a response to a user query regarding physiologic information). In an example, the symptom status for the one or more symptoms 620 can include indices, metrics, or other measures corresponding to the symptom status. In certain examples, the indices, metrics, or other measures can include a dyspnea score (e.g., rating a severity of shortness of breath), a fluid overload index (e.g., "wetness," rating a severity of pulmonary edema or another symptom involving fluid retention), a fatigue index (e.g., rating a perceived level of exercise tolerance, ease of performing physical activity, or other measure of endurance or fatigue), a cardiac output index (e.g., rating a left ventricular ejection fraction, a left ventricular pumping pressure, a time derivative of a pumping pressure, or other value) or another index, metric, or measure. In certain examples, one or more of the indices, metrics, or other measures can include one or more data values, one or more trends, one or more statistics (a maximum, minimum, moving average, weighted average, median, mean, or another central tendency), one or more rates of change, or other information. In certain examples, the symptom status for one or more symptoms 620 can be further subdivided, or can refer to one or more subcategories. For example, dyspnea can include one or more of dyspnea-on-exertion (e.g., a shortness of breath during physical activity), dyspnea-at-rest, nocturnal paroxysmal dyspnea (e.g., a transient shortness of breath or labored breathing during nighttime, or during sleep), orthopnea (e.g., a shortness of breath or labored breathing depending on whether a person is standing upright or lying down), dyspnea-on-anxiety, or one or more other subdivisions or subcategories of dyspnea. Similarly, in certain examples, other symptoms, such as the fluid overload index or a weight change, can include one or more of pulmonary edema, generalized edema, peripheral edema, a positive weight change, a negative weight change, etc. In an example, a symptom status including an onset of pulmonary edema can be derived (e.g., a fluid overload index relating to an abnormal retention of fluid in the lungs or bronchi), such as by using physiologic information 610 from the intrathoracic impedance sensor 222 shown in FIG. 2. In an example, a symptom status including a degree of exercise tolerance can be derived by monitoring a physiologic response to physical activity ("PRA") (e.g., by using an accelerometer 220 as shown in FIG. 2) and by monitoring a corresponding respiration sensor 214 (e.g., as shown in FIG. 2 (e.g., to sense respiration rate information)) or an ECG sensor 212 (e.g., as shown in FIG. 2 (e.g., to sense heart rate information)).

In certain examples, a first fuzzy logic inference, a first neural network, a first set of "crisp" boolean rules, or one or more other decision making techniques can be used to derive a symptom status for one or more symptoms 620 using the physiologic information 610. In certain examples, a second fuzzy logic inference, a second neural network, a second set of "crisp" boolean rules, or one or more other decision making techniques can be used to derive a disease status for one or more diseases 630 using the symptom status for one or more symptoms 620 (e.g., in a cascaded manner). In certain examples, the disease status for one or more diseases 630 can include a heart failure ("HF") disease status, such as an onset of acute heart failure decompensation status, or another disease status (e.g., diabetes).

Figure 7:
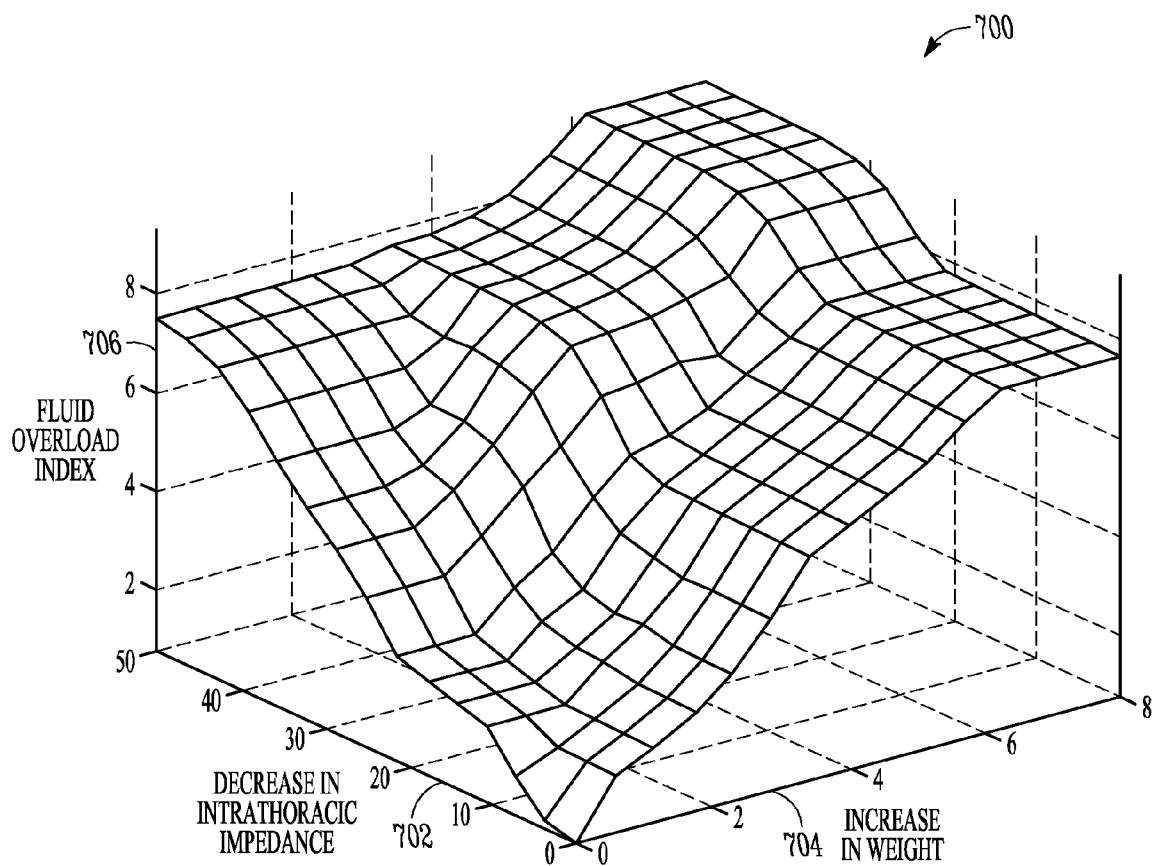
FIG. 7 illustrates generally an example of a surface plot illustrating a relationship between two input variables and an output variable.

FIG. 7 illustrates generally an example of a surface plot 700 illustrating a relationship between two input variables, such as an intrathoracic impedance decrease 702 and a weight decrease 704, and an output variable, such as a fluid overload index 706. In an example, a symptom status can include the fluid overload index 706, and can be derived using a first fuzzy logic inference using a mapping to a first set of fuzzy logic membership functions the physiologic information including the intrathoracic impedance decrease 702 and the weight decrease 704. In this example, the information contained in the surface plot 700 can be included in a set of fuzzy logic rules (e.g., the first fuzzy logic inference can provide a result substantially similar to a result derived instead using a look-up table containing a set of data values describing the surface plot 700). In an example, the fluid overload index 706 can depend on one or more additional inputs. In certain examples, a dimensionality problem can arise when the number of inputs becomes larger. The present inventors have recognized, among other things, that the processing and storage used in performing the mapping or fuzzy logic inference can be less than the processing and storage used in performing a table look-up of the fluid overload index, and that a processing and storage benefit can increase as the number of inputs increases.

In certain examples, one or more inputs to one or more other surface plots can include a status of one or more symptoms, and the resulting output can include a disease status for one or more diseases. In certain examples, one or more of the surface plots can be used as a template to train, define, develop, create, modify, or otherwise influence a set of fuzzy logic rules or membership functions (e.g., based on experimental, observed, or historical data obtained from one or more patients, from a single patient over time, or from another source).

Figure 8:
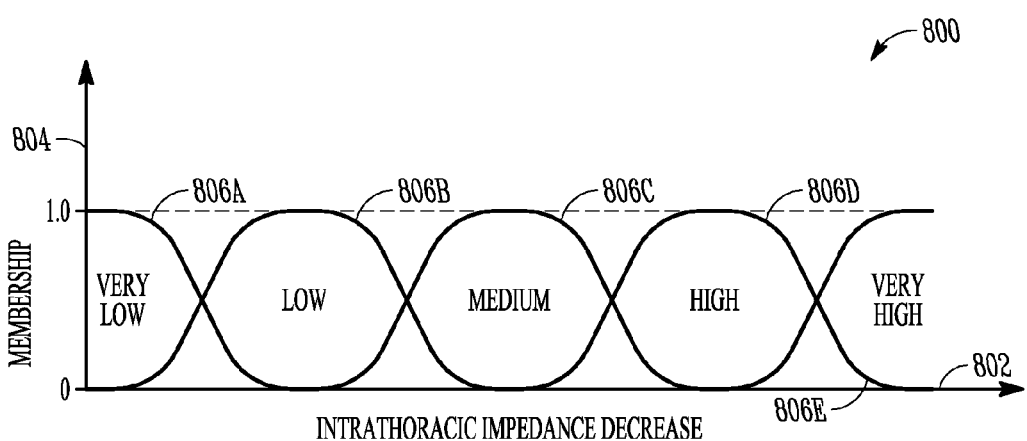
FIG. 8 illustrates generally an example of a map illustrating a relationship between an input variable and a plurality of fuzzy logic membership functions categorized by linguistic terms.

FIG. 8 illustrates generally an example of a map 800 illustrating a relationship between an input variable 802 and a plurality of fuzzy logic membership functions categorized by linguistic terms. In certain examples, one or more membership functions can be defined and need not overlap. In the example of FIG. 8, the membership functions can include a "very low" function 806A, a "low" function 806B, a "medium" function 806C, a high function 806D, and a "very high" function 806E. In certain examples, one or more membership functions can be a constant, or linear across a range of input variable 802 values. In an example, physiologic information (e.g., a data value from one or more sensors) can be mapped to a set of first fuzzy logic membership functions (e.g., a map 800, or some other mapping). In an example, a status of one or more symptoms can be mapped to a second set of fuzzy logic membership functions (e.g., a map 800, or some other mapping).

In certain examples, one or more output functions (e.g., discussed in FIG. 5) can be defined similarly to the membership functions shown in the map 800, or according to one or more other examples discussed in relation to one or more other membership functions. In certain examples, one or more fuzzy logic rules can relate one or more input variables (e.g., the input variable 802) to one or more output functions. In an illustrative example, using the surface plot 700 as a template, a set of fuzzy logic rules can be defined a fuzzy set of output functions (e.g., including information about a fluid overload index 706) to two fuzzy sets of input functions (e.g., a decreasing intrathoracic impedance 702 mapped to a set of fuzzy logic membership functions, such as a map 800, and an increasing weight 704 can be mapped to a different set of fuzzy logic membership functions). In this example, if the decreasing intrathoracic impedance 702 is zero (e.g., no decrease), and the increasing weight 704 is zero (e.g., no increase), then the fluid overload index 706 can be read off as zero. In this example, after mapping, the decreasing intrathoracic impedance 702 can be a member of the "very low" function 806A, and the increasing weight 704 can be a member of the "very low" function 806A. The resulting output function can follow the template 700, and can map to an output "very low" function 806A. In this example, a fuzzy logic rule can be correspondingly defined in linguistic terms stating "IF intrathoracic impedance decrease is VERY LOW AND weight increase is VERY LOW THEN fluid overload index is VERY LOW." In certain examples, the decreasing intrathoracic impedance 702 value, the increasing weight 704, or other values need not be members of only one membership function. In an illustrative example, the decreasing intrathoracic impedance 702 can be a member of both the "high" function 806D and the "very high" function 806E (e.g., the input variable 802 value can be mapped to two membership functions under a non-zero portion of both membership functions). In contrast to this example, if "crisp" boolean rules were used instead of the one or more fuzzy logic rules, then the decreasing intrathoracic impedance 702 can be assigned only one linguistic description (e.g., "very high," or "high," but not both "very high," and "high.")

Figure 9:
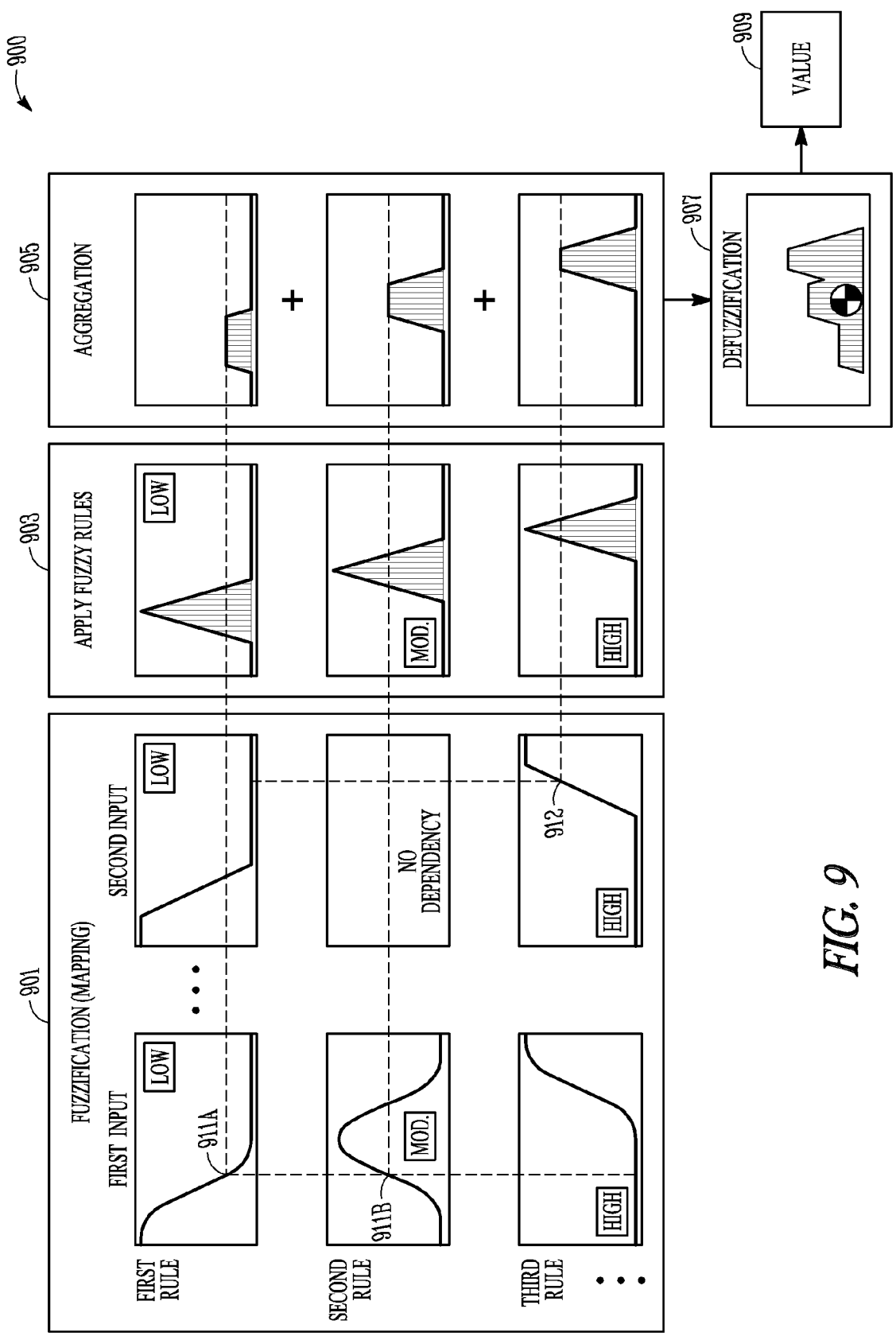
FIG. 9 illustrates generally an example of a method for deriving an output value using a fuzzy logic inference.

FIG. 9 illustrates generally an example of a method 900 for deriving an output value using a fuzzy logic inference, such as by a using a processor 102 including a first fuzzy logic inference module 108A or a second fuzzy logic inference module 108B, or one or more other modules. In this example, two input variables and three rules can be used. In other examples, other numbers of input variables or rules can be used. In this example, the rules can be described in linguistic form as a first rule, such as "IF first input is LOW OR second input is LOW THEN output is LOW," a second rule, such as "IF first input is MODERATE THEN output is MODERATE," and a third rule, such as "IF first input is HIGH OR second input is HIGH THEN output is HIGH." In this example, the second rule has no dependency on the second input. In certain examples, one or more rules, inputs, or output values can be used.

In the example of FIG. 9, at 900, a fuzzification of the first and second inputs can be performed, (e.g., via a mapping to one or more membership functions as shown in FIG. 5, or FIG. 8, or using one or more other techniques). In this example, all of one or more fuzzy logic rules can be applied exhaustively to all of one or more inputs. In certain examples, the one or more input values can correspond to a zero-valued region of the one or more fuzzy membership functions. In these examples, the one or more input values can be called "non-members" of the one or more fuzzy membership functions. In an example, at 903, the first, second, and third rules can be applied to the mapped input variables. In this example, the fuzzy "OR" operator can be performed by taking a maximum of the set of membership functions of which the first and second inputs are members. In this example, in the applying the first rule (e.g., a first row in the example of FIG. 9), the taking the maximum of the two membership functions can be an output function corresponding to a result of "low." Such as result can be called a "consequent," and the set of membership functions of which the first and second inputs are members can be called "antecedents." In this example, the second and third rules can be applied, and at 903 a result of applying the fuzzy logic rules can be a set of one or more output functions. In this example, at 911A, a first input value can intersect a "low" fuzzy logic membership function, at 911B, the first input value can intersect a "moderate" fuzzy logic membership function, and at 912, a second input value can intersect a "high" fuzzy logic membership function. In certain examples, one or more other fuzzy logic operators can be used (e.g., a fuzzy logic operator of "AND" can be taking the minimum of a set of one or more membership functions, or some other operator can be used).

In certain examples, one or more values of a fuzzy logic membership function or other value can be used to modify one or more of the output functions. This modification of one or more output functions can be called an "implication." In the example of FIG. 9, at 905, an implication can be performed using the maximum value of a membership function at an intersection such as at 911A, 911B or 912 to truncate one or more output functions. In certain examples, one or more implications can use one or more values of a first or second input, or a fuzzy logic membership function to truncate, or scale the output function, or to perform another operation on the output function.

In an example, at 905, after the implication (if any), the output functions can be aggregated into one or more aggregate functions. At 907, a single aggregate function can be defuzzified to determine a value 909. In an example, the value can be mapped to a second set of one or more membership functions for reporting to a user, or for use in another different fuzzy logic inference, or other decision making scheme. In an example, a centroid calculation can be used to derive a value 909 from the aggregate function. In an example, defuzzifying the aggregate function can include determining a centroid, a bisector, a maximum (e.g., an absolute maximum, a local maximum, or one or more other extrema), or one or more other methods.

In certain examples, the method of FIG. 9 can be used to derive physiologic information from one or more sensors, a status of one or more symptoms from physiologic information obtained from one or more sensors, a status of one or diseases from the previously derived status of one or more symptoms, or for one or more other inferences related to a determination of a disease status. In certain examples, one or more resulting values (e.g., the value 909) or trends, one or more sets of fuzzy logic membership functions, one or more output functions, one or more aggregate functions, "crisp" or fuzzified physiologic information, or other information from the fuzzy logic inference method can be reported, displayed, communicated, or used in generation of an alert, warning, or alarm to one or more users. In certain examples, a trend (e.g., a plot of one or more values measured over time (e.g., daily or over one or more other intervals), or with respect to one or more other parameters) of the status of physiologic information from one or more sensors, the status of one or more symptoms, or the status of one or more diseases can be reported, displayed, communicated, or used in generation of an alert, warning, or alarm to one or more users.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), or the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
   a physiologic monitor configured to obtain physiologic information about a patient; and
   a processor coupled to the physiologic monitor and configured to receive the physiologic information about the patient, the processor comprising:
   a symptom status detector including a first fuzzy logic inference module configured to derive a symptom status from the physiologic information using a first fuzzy logic inference; and
   a disease status detector coupled to the symptom status detector, the disease status detector including a second fuzzy logic inference module configured to derive a disease status from the symptom status using a second fuzzy logic inference.

2. The system of claim 1, wherein the disease status detector is configured to detect a heart failure decompensation status.

3. The system of claim 2, comprising a physiologic sensor coupled to the physiologic monitor, wherein the physiologic sensor includes at least one of a weight scale, an electrocardiogram (ECG) sensor, a respiration sensor, a heart sound sensor, a blood pressure sensor, an accelerometer, or an intrathoracic impedance sensor.

4. The system of claim 2, comprising a display coupled to the processor, the display configured to report at least one of the symptom status or the heart failure decompensation status to a user.

5. The system of claim 2, comprising a user input coupled to the processor, the user input configured to receive at least some of the physiologic information from a user in response to a query including whether the patient has experienced at least one of a shortness of breath, an abnormal fatigue, an abnormal pain, an abnormal swelling, a chronic cough, a decreased appetite, or a need for an extra pillow when sleeping.

6. The system of claim 1, wherein the processor comprises a fuzzy logic rule selector configured to select at least one rule using information about whether at least one physiologic sensor is unreliable or unavailable; and
wherein the first fuzzy logic inference module is configured to derive the symptom status in response to and using the at least one selected rule.

7. A method comprising:
obtaining physiologic information about a patient;
mapping the physiologic information to a first set of fuzzy logic membership functions;
deriving a symptom status from the mapping of the physiologic information to the first set of fuzzy logic membership functions using a first fuzzy logic inference;
mapping the symptom status to a second set of fuzzy logic membership functions; and
deriving a disease status from the mapping of the symptom status to the second set of fuzzy logic membership functions using a second fuzzy logic inference.

8. The method of claim 7, wherein the deriving the disease status includes deriving a heart failure decompensation status.

9. The method of claim 8, wherein the obtaining the physiologic information comprises monitoring at least one of an implantable or an external physiologic sensor.

10. The method of claim 9, wherein the obtaining the physiologic information includes obtaining information derived from at least one of a heart rate, a respiration rate, a respiration timing, a blood pressure, a lung tidal volume, a physical activity level, a weight, an intrathoracic impedance, a heart sound timing, or a heart sound magnitude.

11. The method of claim 9, wherein the deriving the symptom status using the first fuzzy logic inference comprises:
selecting a rule using information about whether at least one physiologic sensor is unreliable or unavailable; and
deriving the symptom status using the selected rule.

12. The method of claim 9, comprising:
querying a user for at least some of the physiologic information, wherein the query includes at least one of whether the patient has experienced shortness of breath, abnormal fatigue, abnormal pain, abnormal swelling, a chronic cough, a decreased appetite, or a need for an extra pillow when sleeping; and
receiving a user response including at least some of the physiologic information.

13. The method of claim 8, wherein the deriving the symptom status includes deriving at least one of a dyspnea score, a fluid overload index, a left ventricular filling pressure index, a fatigue index, or a cardiac output index.

14. The method of claim 8, comprising displaying at least one of the symptom status or the heart failure decompensation status to a user.

15. The method of claim 8, comprising providing an alert to a user when the heart failure decompensation status indicates an onset of acute heart failure decompensation.

16. The method of claim 7, wherein at least one membership function included in the first or second sets of fuzzy logic membership functions is categorized by a linguistic term.

17. The method of claim 16, wherein the linguistic term includes at least one of very low, low, medium, high, or very high.

18. The method of claim 16, wherein the linguistic term classifies at least one of the physiologic information or the symptom status by a degree of change from a baseline.

19. The method of claim 16, wherein the linguistic term classifies at least one of the physiologic information or the symptom status by a rate of change.

20. The method of claim 7, wherein at least one of the first or second fuzzy logic inferences uses at least one rule based on information obtained from historical patient data.

* * * * *